United States Patent
Abrahams

(10) Patent No.: US 8,679,088 B2
(45) Date of Patent: Mar. 25, 2014

(54) CRANIAL EVACUATION SYSTEM AND USE THEREOF

(76) Inventor: John M. Abrahams, Scarsdale, NY (US)

( * ) Notice: Subject to any disclaimer, the term of this patent is extended or adjusted under 35 U.S.C. 154(b) by 0 days.

(21) Appl. No.: 13/494,582

(22) Filed: Jun. 12, 2012

(65) Prior Publication Data
US 2012/0323217 A1   Dec. 20, 2012

Related U.S. Application Data

(60) Provisional application No. 61/496,803, filed on Jun. 14, 2011.

(51) Int. Cl.
*A61M 31/00* (2006.01)

(52) U.S. Cl.
USPC ...... 604/506; 604/164.11; 604/500; 604/508; 604/509

(58) Field of Classification Search
USPC ............... 604/93.01, 96.01, 102.01, 102.03, 604/103.01, 104, 165.1, 164.11, 174–175, 604/500, 506, 508, 509
See application file for complete search history.

(56) References Cited

U.S. PATENT DOCUMENTS

| | | | |
|---|---|---|---|
| 3,017,887 A | 1/1962 | Heyer | |
| 4,619,261 A | 10/1986 | Guerriero | |
| 5,429,582 A * | 7/1995 | Williams | 600/2 |
| 5,545,176 A | 8/1996 | Murtfeldt | |
| 6,093,187 A | 7/2000 | Lecuyer | |
| 6,306,154 B1 | 10/2001 | Hudson et al. | |
| 7,799,048 B2 | 9/2010 | Hudson et al. | |
| 7,854,923 B2 * | 12/2010 | Chen et al. | 424/70.27 |
| 2003/0040753 A1 | 2/2003 | Daum et al. | |
| 2005/0143689 A1 | 6/2005 | Ramsey | |
| 2008/0109026 A1 * | 5/2008 | Kassam | 606/190 |

(Continued)

FOREIGN PATENT DOCUMENTS

| | | |
|---|---|---|
| EP | 2174602 A1 | 4/2010 |
| WO | WO-2009117353 | 9/2009 |
| WO | WO-2009149398 A2 | 12/2009 |
| WO | WO-2012048023 | 4/2012 |

OTHER PUBLICATIONS

Cabantog et al., "Complications of first craniotomy for intra-axial brain tumour," Canadian Journal of Neurosurgery Science, vol. 21, No. 3, pp. 213-218, Aug. 1994.

(Continued)

*Primary Examiner* — Quynh-Nhu H Vu
*Assistant Examiner* — Larry R Wilson
(74) *Attorney, Agent, or Firm* — Goodwin Procter LLP

(57) ABSTRACT

The present invention relates to a method and device for removing solid matter from a brain and controlling bleeding associated with the removal of the matter. The method involves securing a cranial anchor to a region of the skull in which an opening has been created to expose brain matter and introducing through a passage defined by the anchor a channel member that displaces brain tissue and exposes the solid matter. After removing the solid matter, a flowable hemostat is introduced into the cavity created by removal of the matter. A balloon introduced into the working channel is then inflated to compress the hemostat against the wall of the cavity to control bleeding from blood vessels around the cavity. The device includes a cranial anchor, a channel member defining a working channel, an optional removable trocar, and a catheter for introducing the hemostat and the inflatable balloon into the cavity.

15 Claims, 13 Drawing Sheets

(56) References Cited

U.S. PATENT DOCUMENTS

| | | |
|---|---|---|
| 2008/0275466 A1 | 11/2008 | Skakoon |
| 2009/0048610 A1 | 2/2009 | Tolkowsky et al. |
| 2009/0248056 A1 | 10/2009 | Gabel et al. |

OTHER PUBLICATIONS

Engh, et al., "Endoscopic port surgery for colloid cyst resection: The best of both worlds?," University of Pittsburgh Neurosurgery News, vol. 13, No. 2, p. 4, (May 2012).

Fiss et al., "Use of gelatin-thrombin matrix hemostatic sealant in cranial neurosurgery," Neurosurgery Medical Chir (Tokyo) 47: pp. 462-467, Oct. 2007.

Gazzeri et al., "Hemostatic matrix sealant in neurosurgery: a clinical and imaging study," Acta Neurochirurgie, vol. 153, pp. 148-155, Aug. 2010.

Johanson et al., "Management of massive postpartum haemorrhage: use of a hydrostatic balloon catheter to avoid laparotomy," British Journal of Obstetrics and Gynaecology, vol. 108, pp. 420-422, Apr. 2001.

Miller et al., "Frameless stereotactic aspiration and thrombolysis of deep intracerebral hemorrhage is associated with reduced levels of extracellular cerebral glutamate and unchanged lactate pyruvate ratios," Neurocritical Care, vol. 6, No. 1, pp. 22-29, Feb. 2007.

Sawaya et al., "Neurosurgical Outcomes in a Modern Series of 400 Craniotomies for Treatment of Parenchymal Tumors," Neurosurgery, vol. 42, No. 5 pp. 1044-1056, May 1998.

Wu et al., "Iron and iron-handling proteins in the brain after intracerebral hemorrhage," Stroke, vol. 34, pp. 2964-2969, Dec. 2003.

Wu et al., "Minimally Invasive Procedures for Evacuation of Intracerebral Hemorrhage Reduces Perihematomal Glutamate Content, Blood-Brain Barrier Permeability and Brain Edema in Rabbits," Neurocritical Care, vol. 14, pp. 118-126, Dec. 2010.

Xi et al., "Pathophysiology of brain edema formation," Neurosurgery Clinics of North America, vol. 13, pp. 371-383, Jul. 2002.

Engh, et al., "Neuroendoport surgery facilitates removal of hard-to-reach brain tumors," University of Pittsburgh Neurosurgery News, vol. 10, No. 2, 2 pages, (May 2009).

International Search Report and Written Opinion issued Nov. 12, 2012, for PCT Application PCT/US2012/042067, 15 pages.

\* cited by examiner

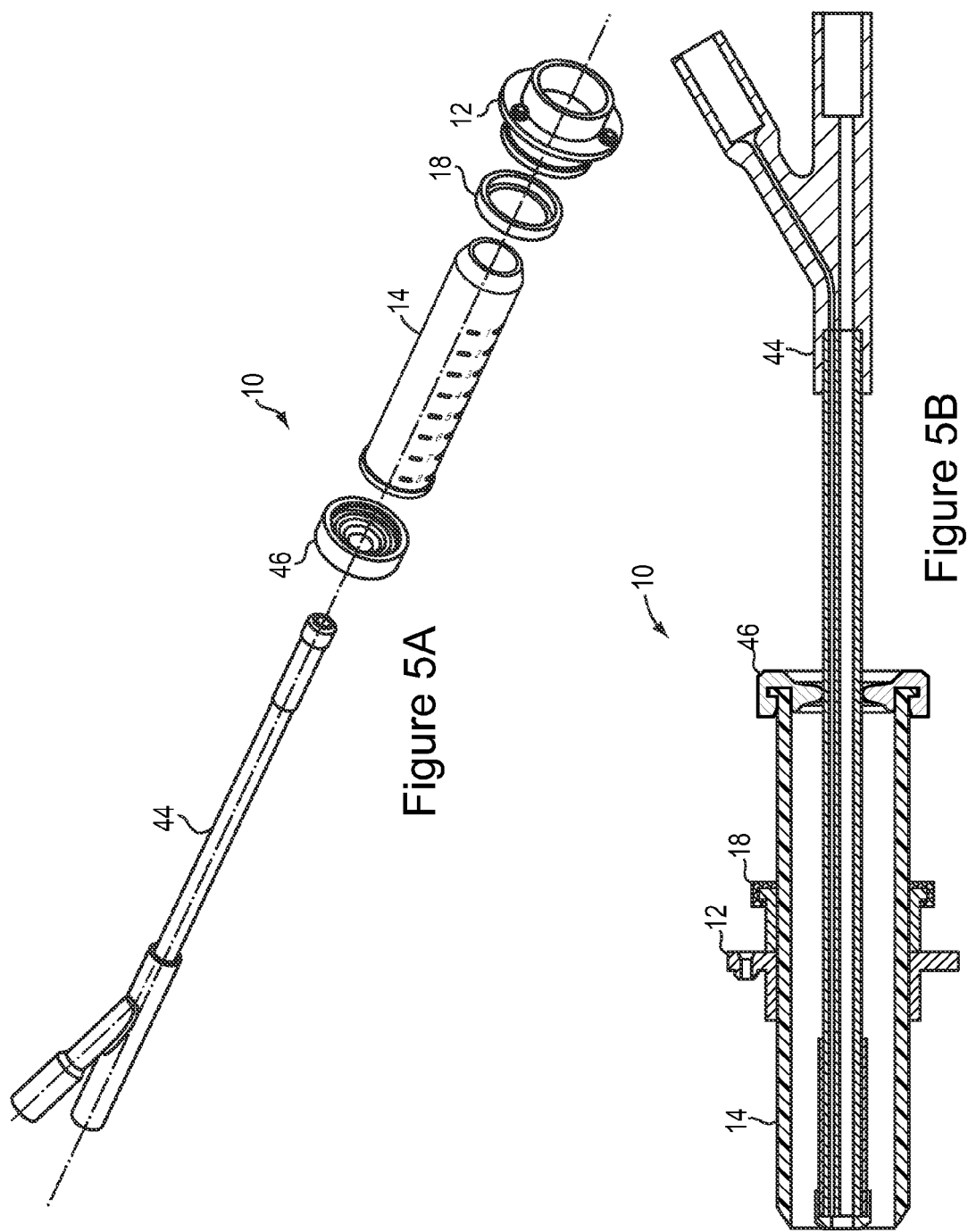

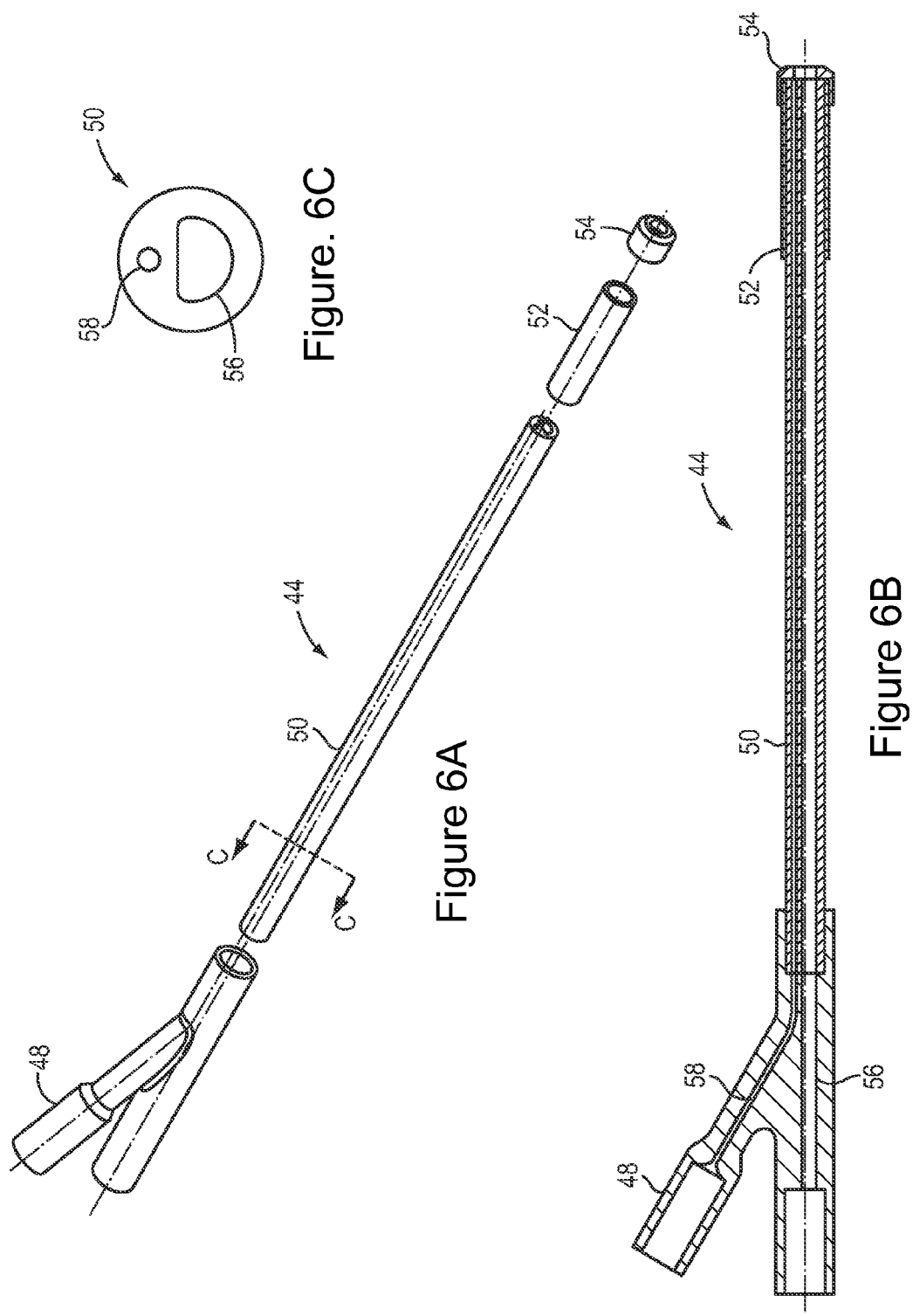

CRANIAL EVACUATION SYSTEM AND USE THEREOF

CROSS-REFERENCE TO RELATED APPLICATION

This application claims the benefit of and priority to U.S. Provisional Patent Application Ser. No. 61/496,803, filed on Jun. 14, 2011, the disclosure of which is incorporated by reference herein in its entirety.

FIELD OF THE INVENTION

The invention relates to a method and system for removing solid matter disposed within brain tissue. More particularly, the invention relates to a method and system for facilitating the removal of solid matter from the brain and for controlling bleeding with a flowable hemostat once the solid matter has been removed.

BACKGROUND

Occasionally undesirable solid matter develops in brain tissue, and can include, a blood clot (also known as an intracranial hemorrhage), tumor tissue, a cyst, a brain lesion or infected brain tissue. Depending upon the size and location of the solid matter, and the condition of the subject, it may be necessary to remove the solid matter via surgical intervention.

Given the fluid, non-self supporting and pliable nature of brain tissue, especially in the brain cortex, one of the problems associated with this type of surgery is that, once the solid matter has been exposed it can be difficult to maintain visual and physical contact of the solid matter in a working cavity because the brain tissue naturally moves or flows into the working cavity and re-covers the solid matter. Furthermore, once the solid matter has been removed, the brain tissue surrounding the cavity created by resection of the solid matter typically tries to flow into the cavity, making it difficult to visualize the cavity (similar to looking into a collapsed bag or balloon). Keeping both the working cavity and the cavity created by removal of the solid matter open for manipulation and visible, especially when trying to identify the source of bleeding, can be difficult if the surgeon is operating without an assistant.

Another problem associated with the surgery is stopping bleeding that occurs once the solid matter has been removed. Typically, the working cavity is irrigated and then the surgeon looks for the source of blood flowing from the surrounding brain tissue. Often, the surgeon may use one hand to insert a hand-held retractor into the cavity while using the other hand to suction the area while looking for bleeding. Occasionally, the surgeon may use bipolar electrocautery to stop bleeding, which may require releasing the retractor. Alternatively, an absorbent material such as Gelfoam (Pfizer, Inc., New York, N.Y.) soaked in thrombin, can be packed into the cavity. The material may be left in place and irrigated until it peels away from the cavity walls once bleeding has stopped. The process can be repeated until bleeding stops. However, it is important to remove the absorbent material before closing the surgical site.

There remains a need for improved methods and systems to facilitate the removal of solid matter from brain tissue, such as by allowing a surgeon to access a cavity without an assistant, and by providing a way to effectively stop bleeding once the solid matter has been removed.

SUMMARY OF THE INVENTION

In one aspect, the invention provides a method of removing solid matter (for example, tumor tissue, a blood clot, a cyst, a brain lesion, or infected brain tissue (e.g., an abscess or a bacterial or fungal infection)) disposed within brain tissue of a subject, and then controlling bleeding once the solid matter has been removed. The method involves securing a cranial anchor to an opening in a skull of the subject, where the anchor defines an anchor passage running therethrough. Then a channel member is passed through the anchor passage of the anchor to facilitate displacement of brain tissue and to expose the solid matter. The channel member has a first end and a second end and defines a working channel passing through the channel member from the first end to the second end. Optionally, a removable, solid trocar can be inserted into the working channel to displace the brain tissue and to expose the solid matter. The trocar, if used, then is removed to leave the working channel open for subsequent manipulations by the surgeon. The solid matter is removed via the working channel to create a cavity where the solid matter used to reside. In other words, the cavity is defined by the brain tissue that surrounded the solid matter prior to removal of the solid matter. A flowable hemostat is introduced into the cavity via the working channel to contact the brain tissue that surrounded the solid matter prior to its removal. An inflatable balloon introduced via the working channel is inflated such that the wall of the inflated balloon compresses the hemostat against the brain tissue that surrounded the solid matter prior to its removal thereby to stop the bleeding from blood vessels disposed within the brain tissue surrounding the cavity.

The method can also include removing a portion of skull from the subject to create an opening that exposes a region of brain tissue containing the solid matter. Thereafter a cranial anchor is secured to the opening. Furthermore, depending upon the procedure being implemented, the flowable hemostat can be introduced into the cavity before, during, and/or after the inflation of the balloon.

The anchor passage may have an internal diameter of from 1 mm to 100 mm, from 2 mm to 80 mm, from 3 mm to 75 mm, from 4 mm to 65 mm, from 5 mm to 50 mm, from 6 mm to 45 mm, 7 mm to 40 mm, from 8 mm to 35 mm, or from 10 mm to 30 mm. Furthermore, if desired, the channel member can further include a removable, solid trocar disposed within the working channel. The trocar can further facilitate the displacement of brain tissue to expose the solid matter. When a trocar is used, it is removed from the working channel to permit the surgeon to remove the solid matter via the working channel. The working channel can be from 2 cm to 15 cm long, from 3 cm to 12 cm long, from 4 cm to 11 cm long, or from 5 cm to 10 cm long, and can have an internal diameter of between 7 mm and 40 mm, or between 10 mm and 30 mm. The trocar, when used, is dimensioned to be inserted within the working channel.

Depending upon the surgical procedure, a catheter may be inserted into the working channel after the solid matter is removed. The catheter can be a dual lumen catheter that permits the introduction of the hemostat via a first lumen and the introduction of the inflatable balloon via a second lumen. Depending upon the procedure, the balloon can be inflated for 30 seconds to 72 hours, 30 seconds to 48 hours, 30 seconds to 24 hours, 30 seconds to 12 hours, 30 seconds to 6 hours, 30 seconds to 3 hours, 30 seconds to 2 hours, 30 seconds to 1 hour, 30 seconds to 30 minutes, 30 seconds to 20 minutes or 30 seconds to 10 minutes after initial inflation to compress the hemostat against the wall of the cavity. In certain procedures, for example, when there is significant bleeding, the catheter can be left in place within the brain from 12 to 72 hours.

In another aspect, the invention provides a device or system for removing solid matter disposed within brain tissue of a subject and for controlling bleeding once the solid matter has been removed. The device or system includes (a) a cranial anchor defining an anchor passage running therethrough and adapted to be secured to a skull of a subject, (b) a channel member adapted for insertion through the anchor passage of the anchor, wherein the channel member has a first end and a second end and defines a working channel passing through the channel member from the first end to the second end, (c) an optional removable, solid trocar adapted to be introduced within the working channel of the channel member for displacing brain tissue and exposing the solid matter, and (d) a catheter adapted to pass through the working channel optionally once the optional trocar has been removed and to introduce into the brain tissue surrounding the solid matter, once the solid matter has been removed, a flowable hemostat and an inflatable balloon.

In certain embodiments, the anchor passage may have an internal diameter of from 1 mm to 100 mm, from 2 mm to 80 mm, from 3 mm to 75 mm, from 4 mm to 65 mm, from 5 mm to 50 mm, from 6 mm to 45 mm, 7 mm to 40 mm, from 8 mm to 35 mm, or from 10 mm to 30 mm. The anchor can optionally further comprise a flange dimensioned to overlap a region of the skull when the anchor is secured onto the skull adjacent and over an opening in the skull that exposes the brain tissue. The flange can define one or more apertures dimensioned to receive a fastener, for example, a bone screw. In certain embodiments, the working channel is from 2 cm to 15 cm long, from 3 cm to 12 cm long, from 4 cm to 11 cm long, or from 5 cm to 10 cm long, and can have an internal diameter of between 7 mm and 40 mm, or between 10 mm and 30 mm.

In certain other embodiments, the trocar has a proximal end that can be gripped by the surgeon and a distal end for contacting the brain tissue. The distal end can be dimensioned to define a convex brain tissue contacting surface.

The catheter can be a dual lumen catheter that permits the introduction of the hemostat via a first lumen and the introduction of the inflatable balloon via a second lumen. Optionally, the catheter can include an actuator that facilitates introduction of the inflatable balloon into the subject, and/or an actuator for inflating the balloon within the subject, and/or an actuator for introducing the hemostat into the subject.

The foregoing aspects and embodiments of the invention may be more fully understood by reference to the drawings, detailed description and claims.

BRIEF DESCRIPTION OF THE DRAWINGS

FIG. 5A is a schematic, perspective, exploded representation of certain components of a device for removing solid matter from brain tissue in accordance with one embodiment of the invention. FIG. 5B is a schematic, cross-sectional representation of the device depicted in FIG. 5A when assembled.

FIG. 6A is a schematic, perspective, exploded representation of a balloon catheter for use with the device depicted in FIG. 5A. FIG. 6B is a schematic, cross-sectional representation of the balloon catheter depicted in FIG. 6A. FIG. 6C is a schematic, cross-sectional representation of the balloon catheter depicted in FIG. 6A taken along the line C-C.

In FIG. 9D, the balloon is inflated to compress the hemostat against the cavity.

DETAILED DESCRIPTION

The invention relates to a method and device or system for facilitating the removal of undesirable solid matter from brain tissue, and for controlling intracranial bleeding in the region of the brain tissue once the solid matter has been removed.

Figure 1A:
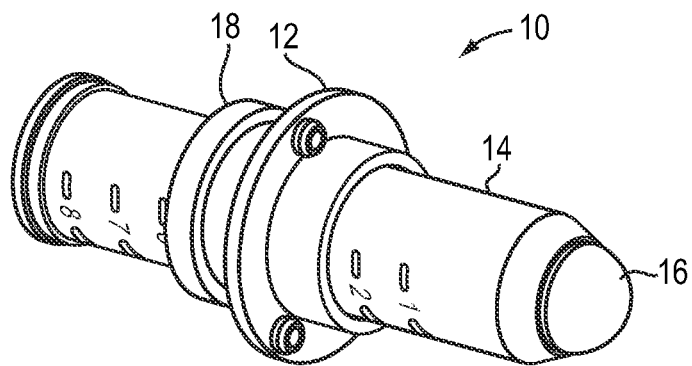
FIG. 1A is a schematic, perspective representation of certain components of a device for removing solid matter in brain tissue in accordance with one embodiment of the invention.
Figure 1B:
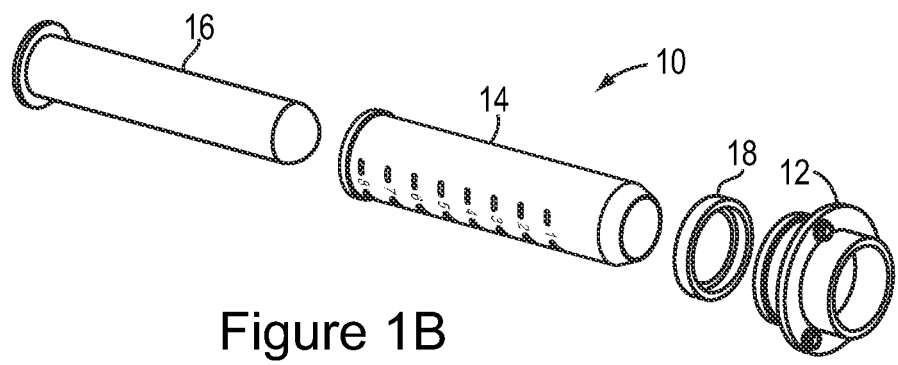
FIG. 1B is a schematic, exploded representation of the components depicted in FIG. 1A.
Figure 1C:
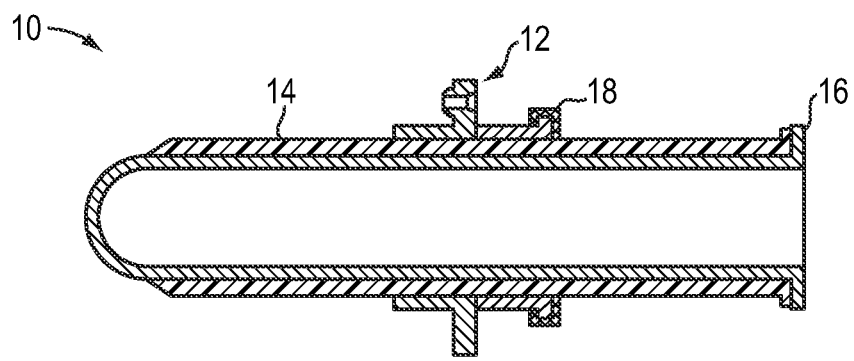
FIG. 1C is a schematic, cross-sectional representation of the device depicted in FIG. 1A.

FIGS. 1A-1C depict a device 10 for providing access to the solid matter (for example, tumor tissue, a blood clot, a cyst, a brain lesion or infected brain tissue) disposed within the brain tissue of a subject. The device 10 includes a cranial anchor 12, a channel member 14, and an optional trocar 16. An anchor seal 18 may optionally be provided as part of the anchor 12. The channel member 14 is dimensioned to fit within an anchor passage of the anchor 12 and to receive the trocar 16. A tight fit between the anchor 12 and the channel member 14 reduces the likelihood that channel member 14 will become misaligned from the anchor 12. The anchor seal 18, when present, can also help stabilize the channel member 14 as it passes through anchor 12. Each of the components is described in greater detail below.

Figure 2A:
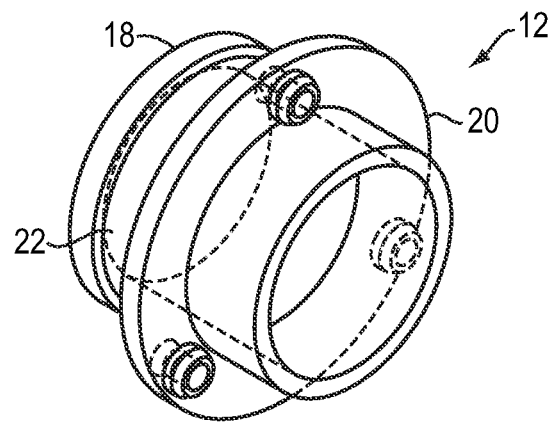
FIG. 2A is a schematic, perspective representation of a cranial anchor for use with the device depicted in FIG. 1A.
Figure 2B:
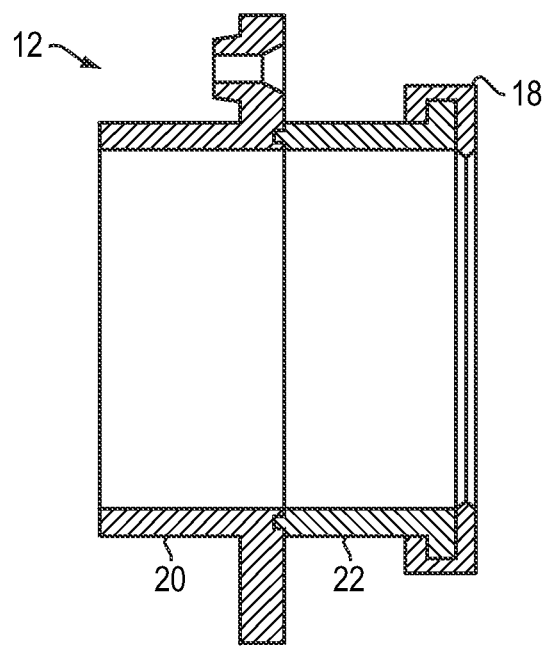
FIG. 2B is a schematic, cross-sectional representation of the anchor depicted in FIG. 2A.

FIGS. 2A-2B depict an assembled anchor 12. The anchor 12 can include the anchor seal 18, as well as a lower anchor portion 20 and an upper anchor portion 22. Each of the components can be substantially cylindrical, or any other set of corresponding and interfitting shapes. When assembled, upper anchor portion 22 can be disposed upon the upper surface of the lower anchor portion 20 such that central axes of the lower anchor portion 20 and the upper anchor portion 22 are coaxial. In another embodiment, the anchor can be a single unitary member containing both the lower anchor portion integral with the upper anchor portion. The anchor seal 18 can be disposed about an outer edge of the upper anchor portion 22 disposed apart from the lower anchor portion 20.

Figure 2C:
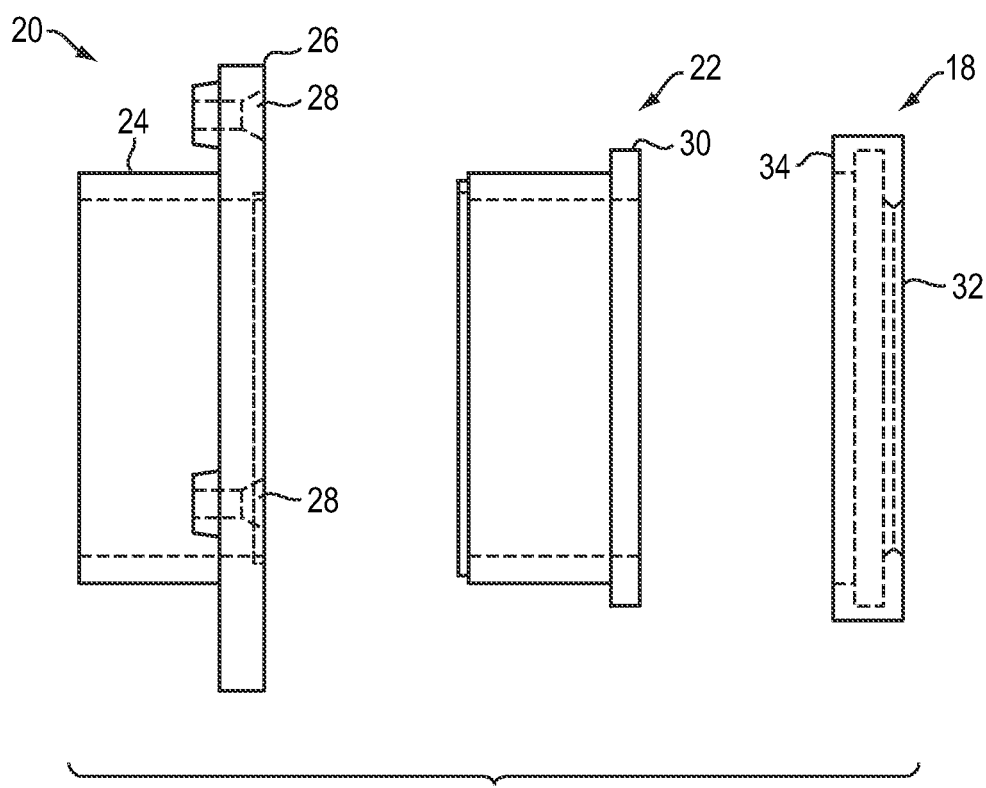
FIG. 2C is a schematic, plan representation of various components of the anchor depicted in FIG. 2A.

As seen in FIG. 2C, the lower anchor portion 20 may have an extended, insert portion 24 and a flange 26. The insert portion 24 can be substantially tubular, defining a passage for receiving the channel member 14, and adapted for insertion through a skull. The boundaries of the flange 26 may extend beyond the boundaries of the insert portion 24, creating a lip member that prevents the upper anchor portion 20 from passing through the opening in the skull. In addition, flange 26 can also define one or more apertures or through holes 28. The apertures 28 are dimensioned to permit a fastener, such as a bone screw, to be passed therethrough and secured to the skull, thereby securing the insert portion 24 to the skull.

The upper anchor portion 22 can be dimensioned to interfit with the lower anchor portion 20, for example, like a cylinder, and can define a passage for receiving the channel member 14. The upper anchor portion 22 can be connected to the lower anchor portion 20 through the interfitting of the two pieces. The channel member 14 is passed through both objects then secured with the anchor seal 18. The upper anchor portion 22 and the lower anchor portion 20 can form an essentially continuous cylindrical anchor passage for receiving the channel member 14. In certain embodiments, an internal diameter of the anchor passage can range from 1 mm to 100 mm, from 2 mm to 80 mm, from 3 mm to 75 mm, from 4 mm to 65 mm, from 5 mm to 50 mm, from 6 mm to 45 mm, 7 mm to 40 mm, from 8 mm to 35 mm, or from 10 mm to 30 mm. An anchor seal receiving member 30 can be included for receiving anchor seal 18. In one embodiment, anchor seal receiving member 30 can be a protrusion around which the anchor seal 18 is wrapped. The lower anchor portion 20 and the upper anchor portion 22 can be manufactured from a variety of materials approved for short term implant applications, including, but not limited to, metals, such as, stainless steel nitinol, cobalt chrome, titanium, and aluminum, plastics, such as, thermoplastic polycarbonate urethane, segmented polyurethane, thermoplastic silicone polycarbonate urethane, polyethylene fiber, thermoplastic polyether urethane, thermoplastic silicone polyether urethane, and ultra high molecular weight polyethylene, blends, such as a polycarbonate/acrylonitrile butadiene styrene (PC/ABS) blends, and other materials with biocompatible coatings, such as the Comfort-Coat coatings available from DSM (Heerlen, the Netherlands). As noted above, in certain embodiments, the anchor 12 can be formed as a single, unitary piece that defines both the lower anchor portion and the upper anchor portion.

The anchor seal 18 can be shaped similarly and adapted to connect to the upper anchor portion 22. The anchor seal 18 can be substantially cylindrical with an upper seal surface 32 and a lower anchor seal surface 34 defining a groove therebetween. The groove can be adapted to fit around the anchor seal receiving member 30 on the upper anchor 22 to secure the anchor seal 18. The upper seal surface 32 can extend inwardly beyond an edge of the inner surface of the upper anchor portion 22 such that the anchor seal 18 extends into the cylindrical passage defined by the lower anchor portion 20 and the upper anchor portion 22. The anchor seal 18 can be made of any of a variety of materials, particularly resilient and elastic materials known in the art, such as silicone rubber, ethylene-propylene, and fluorocarbon. Ideally, the material used is approved for use in medical devices.

In certain embodiments, a rotatable or swivel element (for example a ball socket) can be introduced into and attached to anchor 12. The ball socket can facilitate the movement of channel member 14 within anchor 12. The rotatable or swivel element can optionally further comprise a seal that holds the working channel 14 in place once inserted into the anchor. The rotatable or swivel element permits the surgeon to rotate or otherwise move the channel member 14 as necessary during the surgical procedure.

Figure 3A:
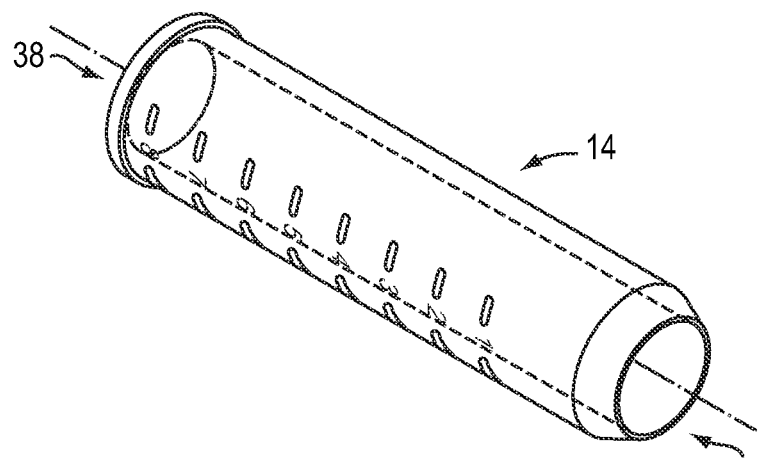
FIG. 3A is a schematic, perspective representation of a channel member for use with the device depicted in FIG. 1A.
Figure 3B:
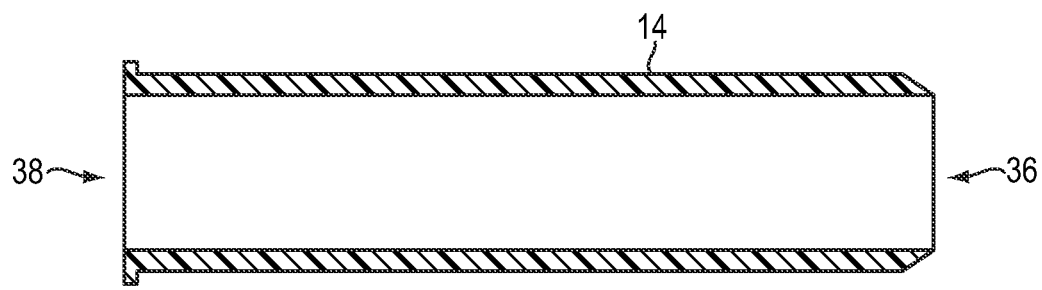
FIG. 3B is a schematic, cross-sectional representation of the channel member depicted in FIG. 3A.

FIGS. 3A-3B depict the channel member 14. The channel member 14 can be any shape, such as a cylindrical shape, that corresponds to and interfits with the anchor passage defined by the anchor 12. A first end (distal end) 36 of the channel member 14 can be adapted for insertion through the anchor passage of the anchor 12. The first end 36 can include a chamfered or otherwise narrowed edge to increase the ease of insertion into the anchor 12, and to push through and separate brain tissue. A second end (distal end) 38 of the channel member 14 opposite the first end 36 can be adapted to remain outside of the skull and external to the anchor 12. The second end 38 can have a flange or ledge extending beyond the outer surface of the channel member 14. The flange can be dimensioned to be larger than the anchor passage of the anchor 12, such that the channel member 14 is restricted from completely passing through the anchor passage and into the brain tissue. The channel member 14 defines a hollow working channel running along its axis between the first end 36 and the second end 38. The working channel is adapted to provide a route for introducing tools (for example, a catheter for introducing a flowable hemostat and/or an inflatable balloon) and reagents (for example, medication, irrigation fluids, a hemostat) to the interior of the skull, and more specifically to the location of the solid matter, as discussed in greater detail below. The working channel may be of a variety of lengths, from 0.5 cm to 30 cm, from 2 cm to 15 cm, or from 5 cm to 10 cm, and have an internal diameter of between 7 mm and 40 mm, or between 10 mm and 30 mm.

In certain embodiments, the channel member 14 can also be dimensioned to a specific size for a specific surgical procedure. Furthermore, an exterior surface of channel member 14 can be marked with uniform graduations so that a user can control the depth of insertion of channel member 14 into the brain tissue as it passes through anchor 12. Channel member 14 can be made of many different materials approved for short term implant use, including, but not limited to, metals, such as, stainless steel, nitinol, cobalt chrome, titanium, and aluminum, plastics, such as, thermoplastic polycarbonate urethane, segmented polyurethane, thermoplastic silicone polycarbonate urethane, polyethylene fiber, thermoplastic polyether urethane, thermoplastic silicone polyether urethane, and ultra high molecular weight polyethylene, blends, such as PC/ABS blends, silicone rubber, such as 70 to 80 durometer, silicon, and other materials with biocompatible coatings, such as the ComfortCoat coatings available from DSM (Heerlen, the Netherlands). The material can be translucent, enabling a surgeon to see the progression of tools and other items further into the anchor, and can be parylene coated.

In certain embodiments, the channel member 14 is adapted to be collapsible, thereby facilitating a single channel member 14 useful with various sized openings to the brain by providing a range of working channel dimensions. To enable collapsibility, the channel member 14 may be substantially the same as previously described but with one or more slits running along a length thereof. Grooves (e.g., 5 mm in width), can be used separately or in conjunction with the slit to further facilitate controlled collapsing of the channel member 14. The slits and/or grooves facilitate limited collapse of the channel member 14, allowing the channel member 14 to conform to its surroundings while retaining sufficient rigidity to keep a path open therethrough. Additionally, the channel member 14 may be made of a material with suitable properties for collapsing and expanding, e.g., silicone.

Figure 4A:
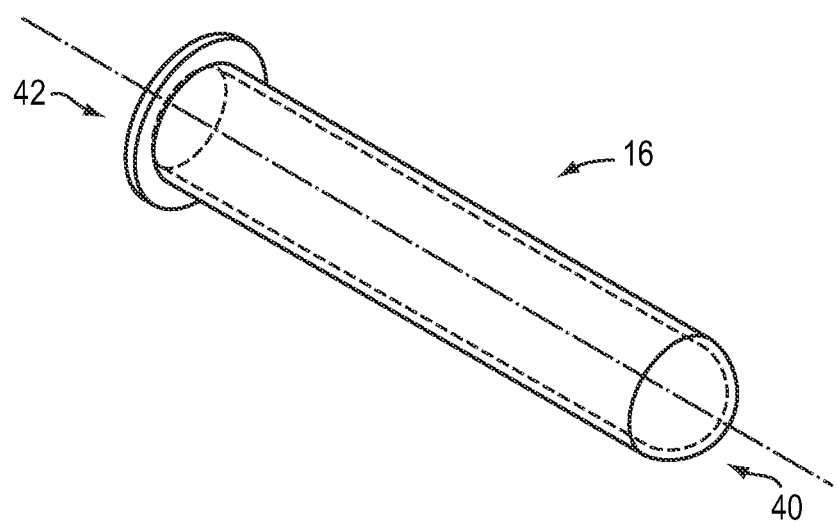
FIG. 4A is a schematic, perspective representation of a trocar for use with the device depicted in FIG. 1A.
Figure 4B:
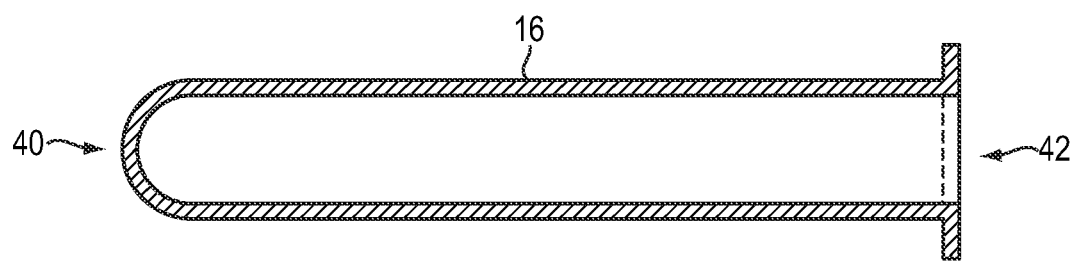
FIG. 4B is a schematic, cross-sectional representation of the trocar depicted in FIG. 4A.

FIGS. 4A-4B depict trocar 16. Trocar 16 can be any shape, but typically will be complementary to and interfit with channel member 14. In some embodiments, trocar 16 will be cylindrical. A first trocar end 40 may be solid or otherwise closed so as to contact and displace the brain tissue while exposing the solid matter. The first trocar end (distal end) 40 can be convex to push brain tissue aside (e.g., a convex brain tissue contacting surface). The trocar 16 initially may be disposed within the channel member 14 to maintain rigidity of the channel member 14 to prevent bending as channel member 14 is inserted into the brain tissue. A second trocar end (distal end) 42 can include a flange with an outer diameter greater than an inner diameter of the channel member 14 to prevent the trocar 16 from completely passing through channel member 14 and into the brain tissue. The distance from the first trocar end 40 to the second trocar end 42 may be greater than the length of the working channel to ensure that the first trocar end 40 extends beyond the first channel member end 36 when the trocar 16 is fully disposed within the channel member 14. In this configuration, brain tissue should be pushed aside by the first trocar end 40 upon insertion. The trocar 16 can be made of many rigid materials suitable for short term implant use including, but not limited to, metals, such as, stainless steel, nitinol, cobalt chrome, titanium, and aluminum, plastics, such as, thermoplastic polycarbonate urethane, segmented polyurethane, thermoplastic silicone polycarbonate urethane, polyethylene fiber, thermoplastic polyether urethane, thermoplastic silicone polyether urethane, and ultra high molecular weight polyethylene, blends, such as a polycarbonate/acrylonitrile butadiene styrene (PC/ABS) blends, and other materials with biocompatible coatings, such as the ComfortCoat coatings available from DSM (Heerlen, the Netherlands). The trocar 16 can be substantially solid, or may define a substantially empty interior volume.

FIGS. 5A-5B depict the device 10 with a catheter 44 and a catheter seal 46 following removal of the trocar 16 from channel member 14. The catheter seal 46 can be placed on the second channel end 38. The catheter 44 can then be inserted into the channel member 14 through the catheter seal 46. This may create a substantially closed environment underneath catheter seal 46, helping to prevent fluid from leaking out of the working channel Catheter 44 can also include one or more actuators to facilitate introduction of a balloon into a subject, inflating a balloon already in the subject, and/or introducing a hemostat into the subject. These actuators may include syringes, air pumps, fluid pumps, and any other actuators suitable for the purposes stated above. The structure of the catheter 44 and the catheter seal 46 are described in greater detail below.

FIG. 6A depicts several possible sections of the catheter 44, such as a dual lumen port 48, a dual lumen shaft 50, a balloon 52 surrounding the dual lumen shaft, and a tip 54. The port 48 can be Y-shaped to facilitate the insertion of separate fluids, reagents, materials or devices with minimal interference. Each prong of port 48 can be in communication with a separate lumen, such that an item passing through a first lumen 56 remains separate from an item passing through a second lumen 58, as depicted in FIG. 6B. For example, a flowable hemostat can be introduced through the first lumen 56 and gas, air or another liquid can be introduced through the second lumen 58 to inflate the balloon to an internal pressure less than approximately 30 mm Hg. An exemplary catheter with a dual lumen structure and a balloon is the Mammosite Balloon Catheter (Hologic, Bedford, Mass.). In certain embodiments, where the balloon 52 is not part of the catheter 44, the balloon 52 can be introduced through the second lumen 58. It is understood that the catheter can be a unitary member containing each of the foregoing sections integral with one another or the catheter can contain a number of discrete sections coupled to one another to form the catheter.

The shaft 50 includes lumens 56, 58 (as shown in FIG. 6C), such that when the shaft 50 is connected to the port 48, the lumens 56, 58 in shaft 50 and port 48 together form two individual and continuous flow paths. One or more holes in fluid communication with the first lumen 56 may be disposed near a distal end of the shaft 50 to allow for a flowable hemostat to reach the cavity created by excision of the solid matter. These holes may be disposed before and/or after the balloon 52 in embodiments where the balloon 52 is part of the catheter 44. Holes in fluid communication with the second lumen 58 can be provided proximate the balloon 52 to allow air to enter and inflate the balloon 52. The shaft 50 may be dimensioned to fit within the working channel (and the catheter seal 46 discussed below) and may be longer than the working channel to permit insertion of shaft 50 while port 48 remains outside of the working channel. Shaft 50 may be substantially cylindrical, or any other shape, such as rectangular or triangular. In certain embodiments, the shaft 50 can be at least 20 or 25 cm in length, which can allow a surgeon to leave catheter 44 within the patient and tunneled through the skin This may be useful if there is a lot of bleeding as it permits the catheter (and inflated balloon) to be left in place for a day or more until bleeding has stopped.

The balloon 52 can be substantially cylindrical, or any other shape complementary to, or interfitting with, the shape of the shaft 50. The edges of the balloon 52 may be attached to the shaft 50 and/or the tip 54 to create an airtight seal to permit the inflation of the balloon upon the introduction of air through a lumen of shaft 50. An adhesive suitable for use in short term implant applications, such as cyanoacrylates, epoxies, light cure adhesives, silicones, and urethanes, amongst others, may be used to create the airtight seal. Other adhering methods, such as friction fits between balloon 52 and another surface (such as the tip 54) can be used. A diameter of the balloon 52 can be as small as 1 mm in an uninflated state, up to a diameter of approximately 14 cm and greater in an inflated state. In certain embodiments, the balloon 52 may have a diameter of up to approximately 14 cm, 12 cm, 10 cm, 8 cm, 6 cm or 4 cm in the inflated state. The actual size of the inflated balloon will vary depending upon the size of the cavity created by the surgical procedure.

The balloon 52 can be made of many materials usable in short term implant applications and capable of expanding upon the application of pressurized air, such as a 30 durometer, high strength, low modulus silicone rubber, 1-10 mil polyurethane, flexible PVC, cross-linked polyethylene, PET, or nylon, amongst other materials. Ideally, the material used is also puncture resistant.

Tip 54 can be adapted to fit over an end of the shaft 50 and/or balloon 52. Tip 54 can be a shape complementary to the shaft 50 and may envelop at least one of the lumens 56 and 58. Tip 54 may also include at least one void to allow for a material (for example, a flowable hemostat) in one of the lumens 56, 58 to exit through an end of the catheter 44. Tip 54, as well as the port 48 and the shaft 50, can be made of a material approved for short term implant use, such as 70 durometer silicone rubber. This material may be translucent to facilitate visual monitoring during use. Other materials, including, but not limited to, metals, such as, stainless steel, nitinol, cobalt chrome, titanium, and aluminum, plastics, such as, thermoplastic polycarbonate urethane, segmented polyurethane, thermoplastic silicone polycarbonate urethane, polyethylene fiber, thermoplastic polyether urethane, thermoplastic silicone polyether urethane, and ultra high molecular weight polyethylene, blends, such as a polycarbonate/acrylonitrile butadiene styrene (PC/ABS) blends, and other materials with biocompatible coatings, such as the Comfort- Coat coatings available from DSM (Heerlen, the Netherlands). It is understood that the catheter 44, in addition to facilitating the introduction of the flowable hemostat, can also be used to introduce one or more therapeutic agents (for example, chemotherapeutic agents, antibiotics, growth factors) and/or dyes (for example, imaging agents) into the cavity. These agents can be introduced, for example, via a separate lumen in the catheter 44 or via lumen 56.

In certain embodiments, the tip 54 can also be adapted to facilitate additional functions, including monitoring intracranial pressure (ICP) at the surgical site. This can be achieved, for example, by placing a pressure transducer at or in the vicinity of tip 54 to provide real time information about ICP during the operation and, if desired, after the operation if the tip 54 is left implanted at the surgical site. The tip 54 and the catheter 44 may also be adapted for use as a drain, thereby facilitating the removal of any unwanted fluid buildup at the surgical site during and after (if the tip 54 and the catheter 44 remain) the operation.

Figure 7A:
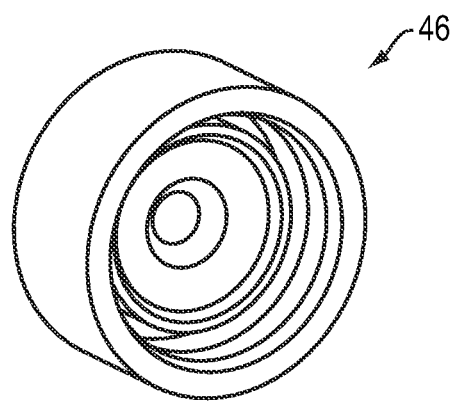
FIG. 7A is a schematic, perspective representation of a seal in accordance with one embodiment of the invention for use with the device depicted in FIG. 5A.
Figure 7B:
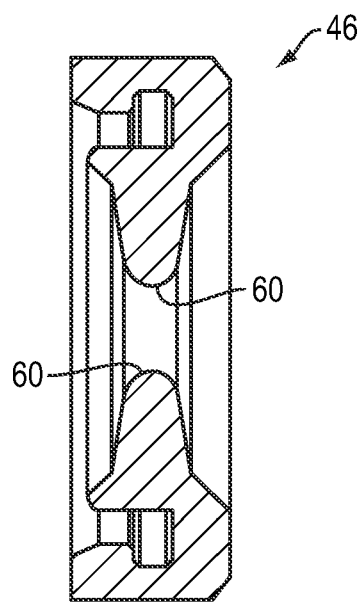
FIG. 7B is a schematic, cross-sectional representation of the seal depicted in FIG. 7A.

The catheter seal 46 (as shown in FIGS. 7A-7B) can help to prevent any substances from escaping the working channel during the surgical procedure. The catheter seal 46 can be disposed on the second end 38 of the channel member 14, such as by fitting around a flange. The catheter seal 46 can be a shape complementary to the channel member 14, which in certain embodiments is cylindrical. While a central portion of the catheter seal 46 can be substantially devoid of structure, a protrusion member 60 can extend from an outer part toward the central portion. The protrusion member 60 can define an aperture through which catheter 44 can be disposed, and the aperture may be dimensioned such that movement of the catheter 44 deflects the protrusion 60, providing an interference fit. The interference fit can prevent a substance or material from escaping between the outside of catheter 44 and the catheter seal 46, and may also increase the stability of the catheter 44 during operation. The protrusion member 60 may be continuous about an inner circumference of the seal 46, or may be divided into two or more separate protrusion members.

Figure 8:
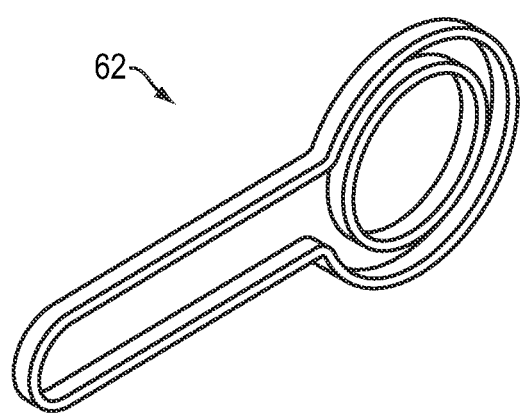
FIG. 8 is a schematic, perspective representation of a template for creating an aperture in the skull of a subject.

FIG. 8 depicts a template 62 corresponding to the size of insert portion 24 of the anchor 12. The template 62 may be used to size a borehole to be drilled through the skull of a subject. The template 62 facilitates the boring of a hole of the right dimension to accommodate anchor 12. Pairing the template 62 with a specific anchor 12 helps ensure this objective is achieved.

Figure 9A:
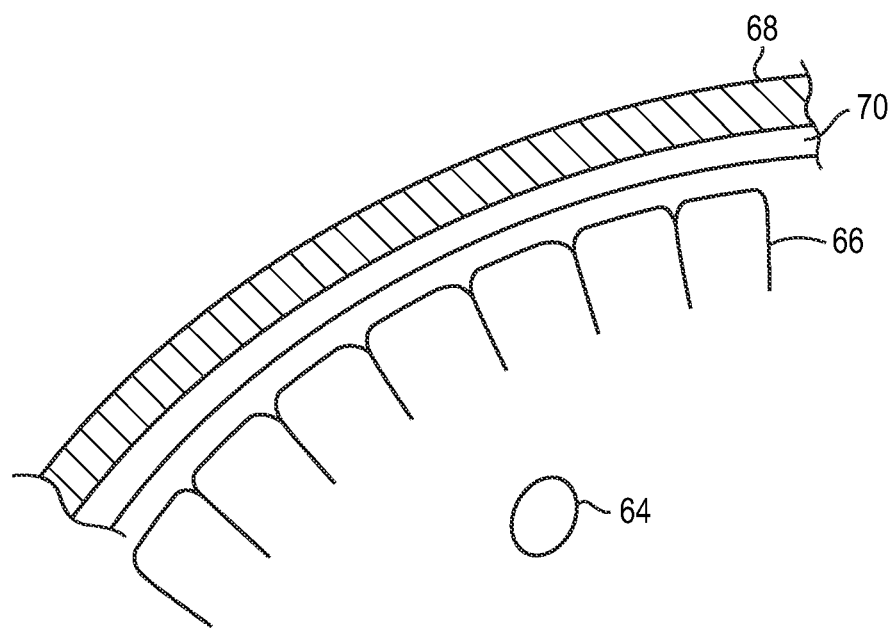
FIG. 9A is a schematic, cross-sectional representation of a solid matter (e.g., a blood clot) in brain tissue.
Figure 9B:
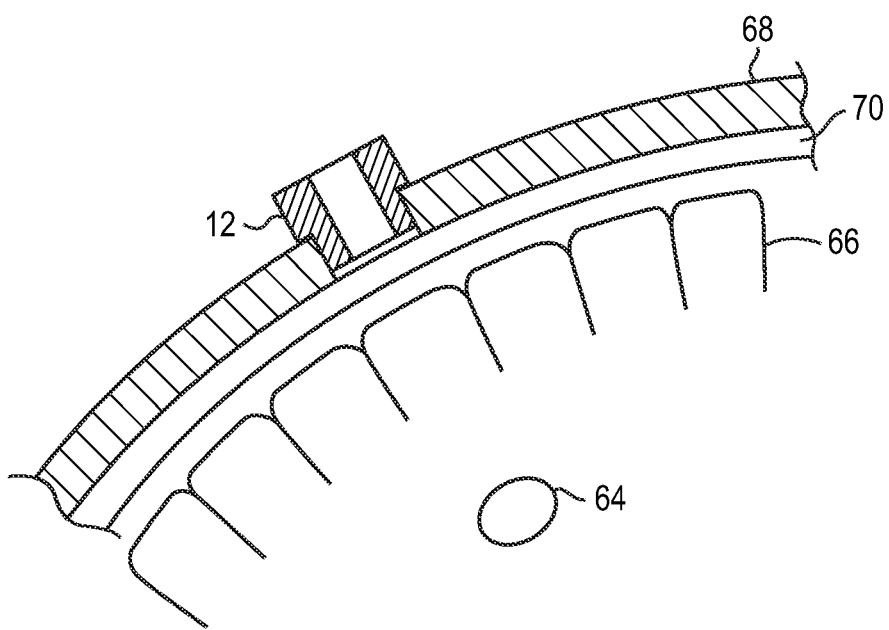
FIG. 9B is a schematic, cross-sectional representation of an anchor disposed within, and secured to the skull to provide access to the solid matter depicted in FIG. 9A.
Figure 9C:
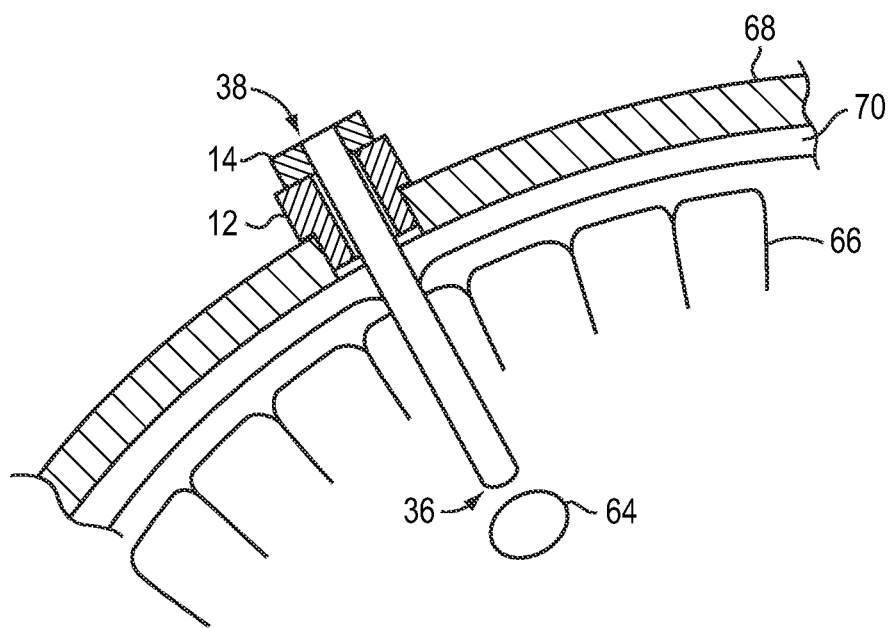
FIG. 9C is a schematic, cross-sectional representation of the anchor and a working channel to provide access to the solid matter depicted in FIG. 9A.

The device 10 described above may be used to remove solid matter 64 (e.g., a blood clot) disposed within brain tissue 66 beneath a subject's skull 68 and dura mater 70, as depicted in FIG. 9A. As depicted in FIG. 9B, once the size and location of the solid matter has been determined, for example, via a preoperative CT scan of the head of the subject, a surgeon can perform a craniotomy using the template to open the skull 68 using a standard drill to allow for the insertion of anchor 12. The anchor 12 may be secured to the skull 68 through the use of one or more bone screws or other fastener through the aperture 28 or a plurality of apertures 28. The anchor 12 defines a passage from the external environment to the interior of the skull 68. FIG. 9C depicts the introduction of the channel member 14 into the interior of the skull 68 to expose the solid matter 64.

Before insertion of the working channel, the surgeon can perform a cortisectomy (i.e., make an opening into the brain) to expose the brain tissue. In this procedure, the dura mater 70 is opened (e.g., with a scalpel or other cutting mechanism) to provide an entry point into the brain tissue 66. The optional trocar 16 can be adapted to be introduced within the working channel of the channel member 14. After the channel member 14 and trocar 16 are introduced through the anchor passage in anchor 12, the first trocar end 42 is passed through the brain tissue 66 and displaces the brain tissue 66 between the anchor 12 and the solid matter 64 to expose the solid matter 64. The first trocar end 42 is moved to the middle or to a side of the solid matter 64. Once the solid matter 64 is exposed, the trocar 16 can be removed creating an open working channel from the first channel end 36 to the second channel end 38 while separating the brain tissue 66 to facilitate the following steps of the procedure. Solid matter 64 can then be removed via the working channel via any known means, such as, with a suction catheter. Depending on the type of solid matter 64, different techniques may be used. For example, if there is a clot present, suction and irrigation can be helpful for removal, whereas a tumor usually requires microdissection.

Figure 9D:
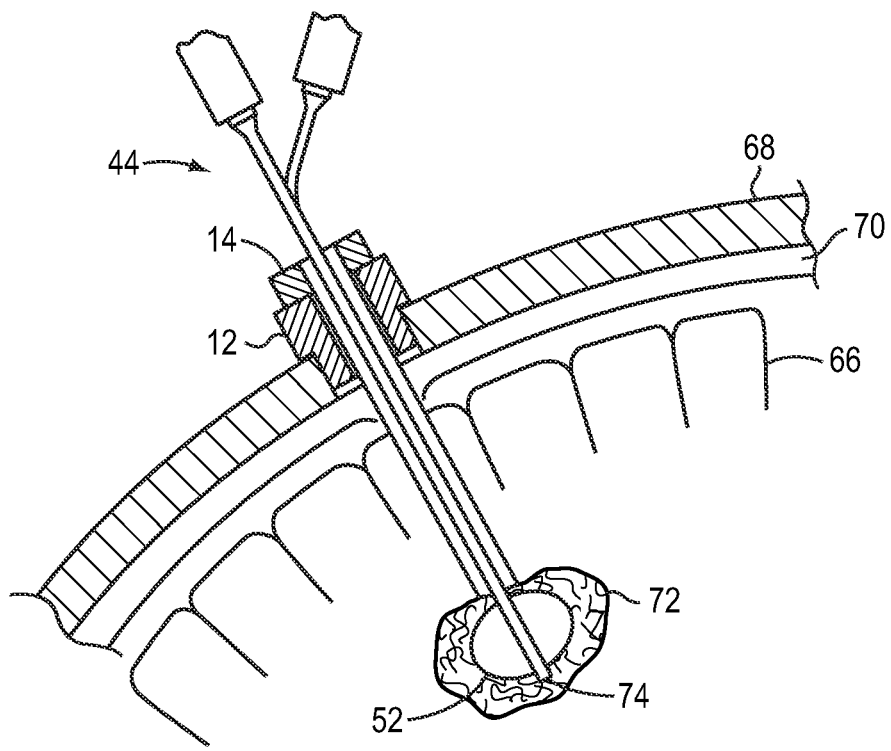
FIG. 9D is a schematic, cross-sectional representation of the use of a balloon and hemostat to stop bleeding in the cavity formed upon removal of the solid matter depicted in FIG. 9A.

Removal of the solid matter 64 creates a cavity 72 (shown in FIG. 9D), and typically results in bleeding from blood vessels in the brain tissue surrounding or defining the cavity. The device 10 can be used to control bleeding. In one embodiment, catheter 44 is optionally inserted through the working channel after removal of the optional trocar 16 so that a distal end is disposed within the cavity 72. In certain embodiments, a rigid stylet, such as a stylet made of stainless steel, can be disposed within catheter 44 during insertion so as to maintain catheter 44 in a substantially linear orientation, thereby lowering the risk that the catheter 44 will become wedged in the working channel. The stylet can then be removed once catheter 44 has been inserted. Catheter 44 can be used to deliver a flowable hemostat 74 into the cavity 72 via the first lumen 56, thereby contacting the brain tissue 66 that originally surrounded the solid matter 64 before its removal with the flowable hemostat 74.

The term "flowable hemostat" is understood to be a liquid hemostatic agent capable of arresting, stemming, or preventing bleeding, preferably by stimulating or inducing blood clotting. Flowable hemostats include, for example, Floseal (Baxter International, Inc., Deerfield, Ill.), Surgiflo (Ethicon, Inc., Somerville, N.J.), Evicel™ sealant delivery system (Johnson & Johnson Wound Management, New Brunswick, N.J.) or the hemostats, described for example, in U.S. Pat. No. 7,854,923.

The catheter 44 can also be adapted to pass optionally a balloon 52 through the working channel and into the cavity 72. The balloon 52 can then be inflated within the cavity 72 by introducing gas, air or other liquid medium through the second lumen 58 whereupon the wall of balloon 52 spreads out and/or compresses the flowable hemostat 74 against the surrounding brain tissue 66. In some embodiments, the flowable hemostat 74 can be injected at the same time, or even after, the balloon 52 is inflated. Depending upon the procedure and the hemostat used, balloon 52 can be inflated for a period of time ranging from 30 seconds to 72 hours, from 30 seconds to 48 hours, from 30 seconds to 24 hours, from 30 seconds to 12 hours, from 30 seconds to 6 hours, from 30 seconds to 3 hours, from 30 seconds to 2 hours, from 30 seconds to 1 hour, from 30 seconds to 30 minutes, from 30 seconds to 20 minutes, from 30 seconds to 10 minutes, after initial inflation. Thereafter, balloon 52 is deflated and catheter 44 is removed from the working channel. When appropriate, the surgeon can deflate the balloon 52 and remove the catheter 44 from the working channel.

In an alternative embodiment, the balloon 52 can be inflated or partially inflated prior to insertion into the cavity 72, particularly in situations where there is concern about the transmission of forces caused by inflating the balloon 52 in the brain. In such situations, balloon 52 is inflated to a predetermined size then introduced through the working channel. When using a compliant material for the balloon 52, the balloon 52 can compress to the size of the working channel before expanding to its predetermined size once outside the working channel and in cavity 72. This technique helps protect against overinflation that may damage the surrounding brain tissue.

The cavity 72 can be irrigated, such as with a normal saline solution, and if there is still evidence of bleeding the process can be repeated, as appropriate. If there is no evidence of bleeding, channel member 14 is withdrawn from the anchor 12, the anchor 12 is then removed from skull 68, and the hole in the skull 68 is then closed. For patients with severe bleeding that is difficult to stop, the surgeon can leave the catheter inserted and balloon 52 inflated for a greater period of time (for example, from 12 to 72 hours). Under such circumstances, catheter 44 can be passed through a separate burr hole in the skull and through a separate stab incision in the skin, and then secured. The original incision to permit insertion of the working channel can be closed by standard surgical procedures. At the appropriate time (for example, from 12 to 72 hours later), the balloon can be removed by deflating the balloon and then pulling the catheter along with the deflated balloon through the burr hole and stab incision. The burr hole and the stab incision can be closed by standard surgical procedures.

In other embodiments, catheter 44 may not include an integral balloon 52. Rather, balloon 52 can be introduced through the second lumen 58, and then inflated with a gas, air or other liquid medium provided through the same or a different lumen. The balloon 52 may be inserted before, during, or after the injection of the flowable hemostat 74. In still other embodiments, catheter 44 may not be used at all. Rather, separate tools or instruments may be introduced into cavity 72 through the working channel to apply the flowable hemostat 74, and to deploy and inflate balloon 52.

In another embodiment, the catheter 44 can be integrally formed with the channel member 14. Several of the components may remain the same, but instead of requiring a separate insertion, the catheter 44 is inserted at the same time as the channel member 14. This simplifies the operation by reducing the number of separate parts and steps required for completion. A flange extending from the surfaces of the channel member 14 can be used to secure the device to the bone, as opposed to relying on a separate anchor. A separate side port in the channel member 44 can be provided to allow removal of the target solid matter.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of removing solid matter disposed within brain tissue of a subject and for controlling bleeding once the solid matter has been removed, the method comprising:
   (a) securing a cranial anchor to an opening in a skull of the subject, the anchor defining an anchor passage running therethrough;
   (b) introducing a channel member through the anchor passage to displace brain tissue and expose the solid matter, wherein the channel member has a first end and a second end and defines a working channel passing through the channel member from the first end to the second end;
   (c) removing the solid matter via the working channel to create a cavity defined by the brain tissue that surrounded the solid matter prior to removal of the solid matter;
   (d) inserting a catheter defining a lumen into the working channel;
   (e) introducing a flowable hemostat through the lumen directly into the cavity to contact the brain tissue that surrounded the solid matter prior to its removal;
   (f) introducing an inflatable balloon into the working channel; and
   (g) inflating the balloon to compress the hemostat against brain tissue defining the cavity to stop bleeding from blood vessels disposed within the brain tissue defining the cavity.

2. The method of claim 1, further comprising the step of, before step (a), removing a portion of skull from the subject to create the opening, which exposes a region of brain tissue containing the solid matter.

3. The method of claim 1, wherein step (d) occurs before, during, or after, step (e).

4. The method of claim 1, wherein the anchor passage of the anchor secured in step (a) has an internal diameter of between 5 mm and 50 mm.

5. The method of claim 4, wherein the anchor passage of the anchor has an internal diameter of between 10 mm and 30 mm.

6. The method of claim 1, further comprising introducing a trocar through the anchor passage.

7. The method of claim 6, wherein the trocar is removed before step (c).

8. The method of claim 1, wherein the working channel introduced in step (b) has a length of from 2 cm to 15 cm.

9. The method of claim 8, wherein the working channel has a length of from 5 cm to 10 cm.

10. The method of claim 1, wherein the catheter is a dual lumen catheter that permits the introduction of the hemostat via a first lumen and the introduction of the inflatable balloon via a second lumen.

11. The method of claim 1, wherein after step (f), the balloon is inflated for 30 seconds to 72 hours.

12. The method of claim 1, wherein after step (f), the balloon is inflated for 30 seconds to 2 hours.

13. The method of claim 1, wherein the solid matter is a blood clot, brain tissue, cyst, or tumor tissue.

14. The method of claim 1, wherein the period of time comprises between 30 seconds and 10 minutes.

15. The method of claim 1, wherein the flowable hemostat is delivered to the cavity through one or more holes in communication with the lumen.

* * * * *